(12) United States Patent
Rioux et al.

(10) Patent No.: US 8,906,017 B2
(45) Date of Patent: Dec. 9, 2014

(54) APPARATUS SYSTEM AND METHOD FOR COAGULATING AND CUTTING TISSUE

(75) Inventors: Robert F. Rioux, Ashland, MA (US); Kathleen Fernald, Brookline, MA (US); Devon Berman, Loudon, NH (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 1597 days.

(21) Appl. No.: 12/269,790

(22) Filed: Nov. 12, 2008

(65) Prior Publication Data
US 2009/0125026 A1      May 14, 2009

Related U.S. Application Data

(60) Provisional application No. 60/987,736, filed on Nov. 13, 2007.

(51) Int. Cl.
*A61B 18/18*      (2006.01)
*A61B 18/14*      (2006.01)
*A61B 18/00*      (2006.01)

(52) U.S. Cl.
CPC ... *A61B 18/1442* (2013.01); *A61B 2018/00065* (2013.01); *A61B 2018/00404* (2013.01); *A61B 2018/00589* (2013.01); *A61B 2018/00601* (2013.01); *A61B 2018/00607* (2013.01); *A61B 2018/0063* (2013.01); *A61B 2018/1412* (2013.01); *A61B 2018/1455* (2013.01); *A61B 2018/1472* (2013.01)
USPC .............................................. 606/52; 606/45

(58) Field of Classification Search
USPC .................................... 606/45–52
See application file for complete search history.

(56) References Cited

U.S. PATENT DOCUMENTS

| | | | |
|---|---|---|---|
| 3,503,398 | A | 3/1970 | Fogarty et al. |
| 4,763,669 | A | 8/1988 | Jaeger |
| 5,584,845 | A | 12/1996 | Hart |
| 5,951,549 | A | 9/1999 | Richardson et al. |

(Continued)

FOREIGN PATENT DOCUMENTS

| | | |
|---|---|---|
| EP | 1 287 788 A1 | 3/2003 |
| EP | 1 532 933 A1 | 5/2005 |

(Continued)

OTHER PUBLICATIONS

PCT International Preliminary Report on Patentability (Chapter I of the Patent Cooperation Treaty) for PCT/US2008/083276, Applicant: Boston Scientific Scimed, Inc., Form PCT/IB/326 and 373, dated May 27, 2010 (7 pages).

(Continued)

*Primary Examiner* — Nathan R Price
(74) *Attorney, Agent, or Firm* — Kacvinsky Daisak Bluni PLLC

(57) ABSTRACT

A combination tissue coagulation and cutting apparatus, system and method for coagulating and cutting tissue. A clamp element includes first and second clamp members having respective first and second porous electrodes, such as sintered metal electrodes. A portion of tissue, such as a blood vessel, is held between the porous electrodes, and fluid from a fluid source can pass through the porous electrodes. The tissue portion can be coagulated when electrical current is applied to the first and second porous electrodes, and an adjustable cutting element that is associated with the clamp members is positioned to cut a segment or all of the coagulated tissue portion. In this manner, the same surgical instrument is used to coagulate and cut tissue.

12 Claims, 14 Drawing Sheets

(56) References Cited

U.S. PATENT DOCUMENTS

| | | |
|---|---|---|
| 6,050,996 A | 4/2000 | Schmaltz et al. |
| 6,277,117 B1 | 8/2001 | Tetzlaff et al. |
| 6,334,861 B1 | 1/2002 | Chandler et al. |
| 7,232,440 B2 | 6/2007 | Dumbauld et al. |
| 7,270,664 B2 | 9/2007 | Johnson et al. |
| 7,276,068 B2 | 10/2007 | Johnson et al. |
| 7,367,976 B2 | 5/2008 | Lawes et al. |
| 2003/0144652 A1 | 7/2003 | Baker et al. |
| 2003/0158549 A1 | 8/2003 | Swanson |
| 2004/0006340 A1 | 1/2004 | Latterell et al. |
| 2005/0112521 A1* | 5/2005 | Harvey et al. .............. 433/1 |
| 2005/0154387 A1* | 7/2005 | Moses et al. .............. 606/51 |
| 2006/0064086 A1 | 3/2006 | Odom |
| 2009/0125012 A1 | 5/2009 | Rioux et al. |
| 2009/0138003 A1* | 5/2009 | Deville et al. .............. 606/33 |

FOREIGN PATENT DOCUMENTS

| | | |
|---|---|---|
| EP | 1 769 765 A1 | 4/2007 |
| WO | WO 01/66026 A2 | 9/2001 |
| WO | WO 01/66026 A3 | 9/2001 |
| WO | WO 02/24089 A1 | 3/2002 |
| WO | WO 03/020339 A2 | 3/2003 |
| WO | WO 03/020339 A3 | 3/2003 |

OTHER PUBLICATIONS

PCT International Preliminary Report on Patentability (Chapter I of the Patent Cooperation Treaty) for PCT/US2008/083270, Applicant: Boston Scientific Scimed, Inc., Form PCT/IB/326 and 373, dated May 27, 2010 (8 pages).

PCT International Search Report for PCT/US2008/083270, Applicant: Boston Scientific Scimed, Inc., Form PCT/ISA/210 and 220, dated Mar. 23, 2009 (8 pages).

PCT Written Opinion of the International Search Authority for PCT/US2008/083270, Applicant: Boston Scientific Scimed, Inc., Form PCT/ISA/237, dated Mar. 23, 2009 (6 pages).

PCT International Search Report for PCT/US2008/083276, Applicant: Boston Scientific Scimed, Inc., Form PCT/ISA/210 and 220, dated Feb. 18, 2009 (6 pages).

PCT Written Opinion of the International Search Authority for PCT/US2008/083276, Applicant: Boston Scientific Scimed, Inc., Form PCT/ISA/237, dated Feb. 18, 2009 (5 pages).

LigaSure Product Brochure, www.ligasure.com/pdf/prod_info/lsligasurevss.pdf (dated Sep. 2004).

Office Communication dated Jun. 22, 2010 in European Patent Application No. 08848871.3-1265 (1 page).

Response to Office Communication dated Aug. 2, 2010 in European Patent Application No. 08848871.3-1269 (12 pages).

* cited by examiner

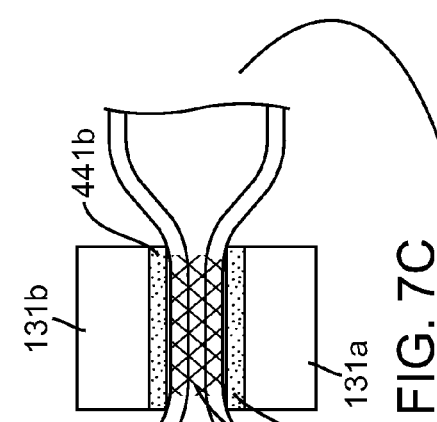
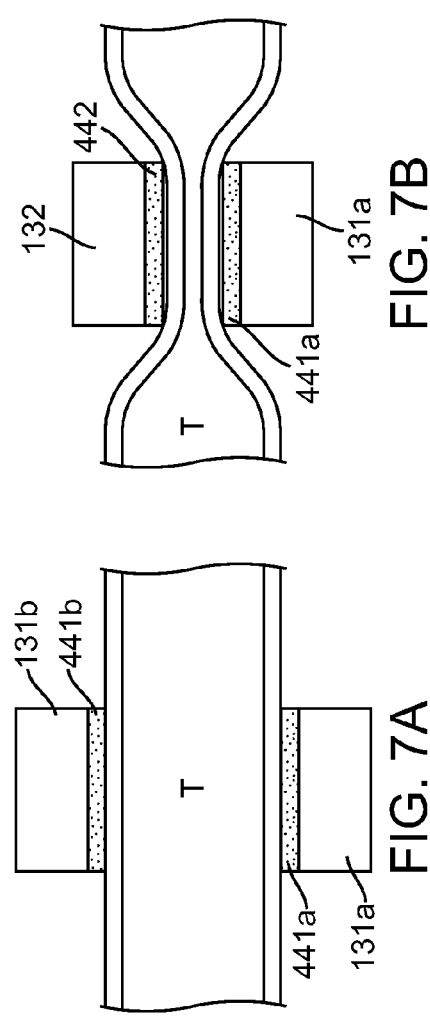

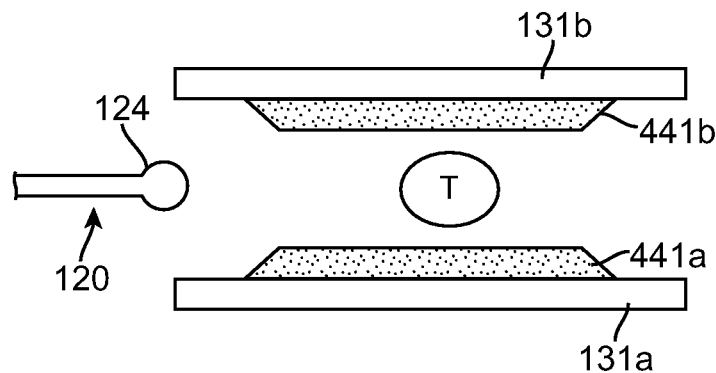
FIG. 8A
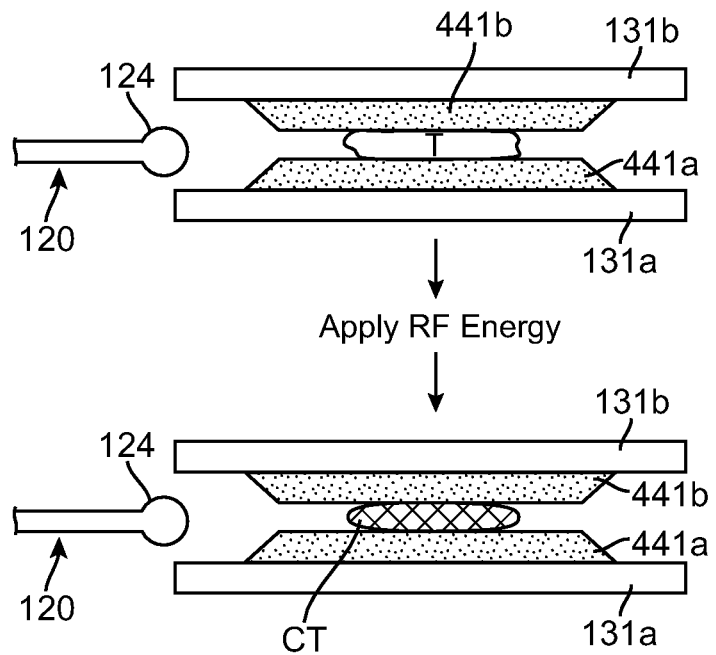
FIG. 8B
FIG. 8C
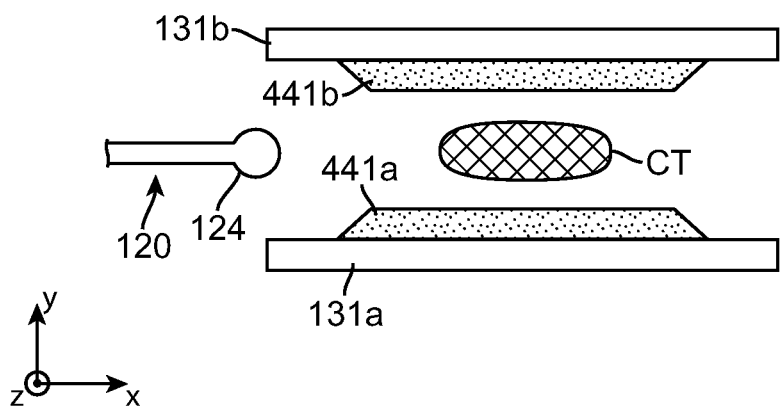
FIG. 8D

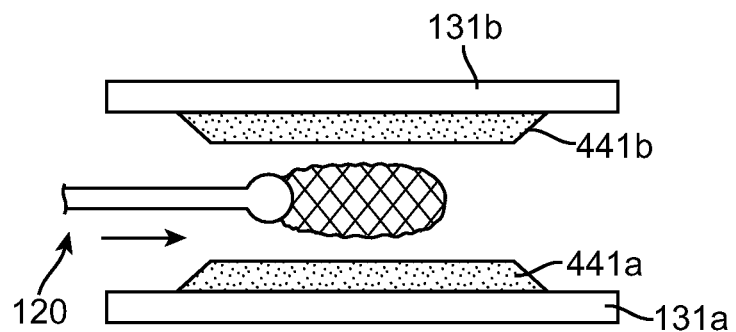
FIG.8E
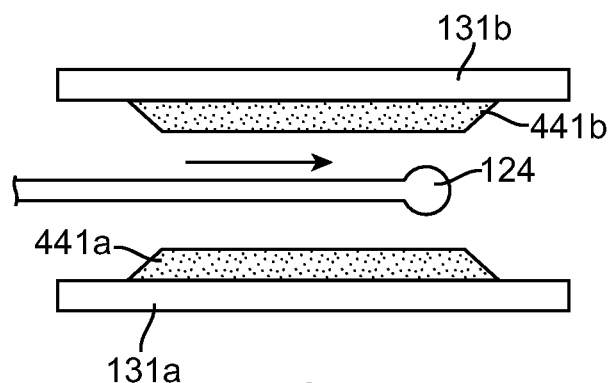
FIG.8F
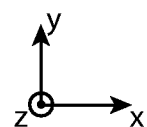

APPARATUS SYSTEM AND METHOD FOR COAGULATING AND CUTTING TISSUE

RELATED APPLICATION

This Application claims priority to U.S. Provisional Patent Application No. 60/987,736 filed on Nov. 13, 2007. The '736 application is incorporated by reference as if set forth fully herein.

FIELD OF INVENTION

The present inventions generally relate to surgical devices that can both coagulate and cut tissue.

BACKGROUND

Electrosurgery is widely used for treating tissue abnormalities. One known electro-surgical device includes a probe having a first or "active" electrode extending from one end. The electro-surgical probe is electrically coupled to an electro-surgical generator, which provides electric current to the treatment site.

When configured as a monopolar device, a second or "return" electrode, having a much larger surface area than the active electrode, is positioned in contact with the skin of the patient. The surgeon may bring the active electrode in close proximity to the tissue, activate a switch, and cause electrical current to arc from the distal portion of the active electrode and flow through tissue to the larger return electrode. When configured as a bipolar device, no return electrode is used. Instead, a second electrode is closely positioned adjacent to the first electrode, with both electrodes being attached to an electro-surgical probe. As with monopolar devices, the electro-surgical probe is electrically coupled to an electro-surgical generator. When the generator is activated, electrical current arcs from the end of the first electrode to the end of the second electrode and flows through the intervening tissue.

Whether arranged in a monopolar or bipolar fashion, the active electrode may be operated to perform a particular function, i.e., to either cut tissue or coagulate tissue. When used to cut tissue, the electrical arcing and corresponding current flow results in a highly intense, localized heating, which breaks intercellular bonds and severs tissue. When used to coagulate tissue, the electrical arcing results in a low level current that denatures cells to a sufficient depth without breaking intercellular bonds. In other words, the low level current does not cut the tissue.

There are many medical procedures in which tissue is cut or carved away for diagnostic or therapeutic reasons. For example, during hepatic transection, one or more lobes of a liver containing abnormal tissue, such as malignant tissue or fibrous tissue caused by cirrhosis, are cut away. Various modalities, including mechanical, ultrasonic, and electrical (e.g., radio frequency or "RF" energy), can be used to resect tissue. Whichever modality is used, extensive bleeding can occur and may obstruct the surgeon's view and lead to dangerous blood loss levels, requiring transfusion of blood. These complications may increase the complexity, time, and expense of the resection procedure.

To prevent extensive bleeding, hemostatic mechanisms, such as blood inflow occlusion, coagulants, and energy coagulation (e.g., electro-surgical coagulation or argon-beam coagulation), can be used. When an electro-surgical coagulation device is used, the bleeding can be treated or avoided by coagulating the tissue in the treatment areas with an electro-coagulator that applies a low level current to denature cells to a sufficient depth without breaking intercellular bonds, i.e., without cutting the tissue. During a typical electro-surgical resection procedure, electrical energy can be conveyed from an electrode along a resection line in the tissue. The electrode may be operated in a manner that incises the tissue along the resection line, or coagulates the tissue along the resection line, which can then be subsequently dissected. In the case where an organ is resected, application of RF energy divides the parenchyma, thereby skeletalizing the organ, i.e., leaving vascular tissue that is typically more difficult to cut or dissect relative to the parenchyma.

When a blood vessel is encountered, RF energy can be applied to shrink the collagen in the blood vessel, thereby closing the blood lumen and achieving hemostasis. The blood vessel can then be mechanically transected using a separate instrument, such as a scalpel or scissors, without fear of blood loss. In general, for smaller blood vessels less than 3 mm in diameter, hemostasis may be achieved within 10 seconds, whereas for larger blood vessels up to 5 mm in diameter, the time required for hemostasis increases to 15-20 seconds. During or after resection of the tissue, RF energy can be applied to any "bleeders" (i.e., vessels from which blood flows or oozes) to provide complete hemostasis for the resected organ.

While known devices and methods have been used effectively in the past, they can be improved. For example, it would be desirable to be able to perform coagulation and cutting functions with the same instrument, thereby eliminating the need for separate instruments and disposing of the need for separate electrode and mechanical cutting devices. A single electro-surgical device that can perform both coagulation and cutting functions during resection procedures would eliminate the need to switch between different surgical devices during surgery and reduce surgery times. Further, it would be desirable to perform electro-surgical resections without charring tissue. When electro-surgically resecting tissue, care must be taken to prevent the heat generated by the electrode from charring the tissue, which generates an undesirable odor, results in tissue becoming stuck on the electro-surgical probe, and increases tissue resistance, thereby reducing the efficiency of the procedure.

SUMMARY

In accordance with one embodiment, an electro-surgical apparatus for coagulating and cutting a portion of tissue includes a clamp element and a cutting element associated with the clamp element. The clamp element includes porous electrodes that are configured to hold and coagulate the tissue portion when electrical current is conducted through the porous electrodes and the tissue portion. The position of the cutting element can be adjusted for cutting of the coagulated tissue portion when electrical current is conducted through the adjustable cutting element and the coagulated tissue.

In another alternative embodiment, a system for coagulating and cutting tissue with the same electro-surgical instrument includes a surgical apparatus for coagulating and cutting tissue, a current source and a fluid source. The tissue coagulation/cutting apparatus has a clamp element that includes porous electrodes that are configured to hold tissue, and a cutting element associated with the clamp element. The position of the cutting element can be adjusted. The current source is electrically coupled to the porous electrodes and the cutting element, and the fluid source is in fluid communication with the porous electrodes. The coagulation/cutting apparatus is configured to coagulate a portion of tissue held between the porous electrodes when fluid passes through the first and second porous electrodes and electrical current is conducted from current source through the porous electrodes and the tissue, and to cut coagulated tissue when electrical current is conducted through the cutting element and the coagulated tissue.

Another embodiment is directed to a method of coagulating and cutting tissue using the same electro-surgical instrument. The method includes holding or securing a portion of tissue between first and second porous electrodes of respective first and second clamping members, and passing fluid through the porous electrodes. Current is applied to the porous electrodes, thereby coagulating the tissue portion held between the porous electrodes. The coagulated tissue portion is cut by applying electrical current to the cutting element.

In one or more embodiments, the clamp element and the cutting element (such as a wire loop) are configured to coagulate the tissue portion (e.g., a blood vessel) and subsequently cut coagulated the coagulated tissue portion, or the tissue portion may be coagulated and cut simultaneously or at about the same time. The entire coagulated tissue portion or a segment thereof can be cut.

Additionally, in one or more embodiments, the clamp element includes first and second clamp members, each of which has a porous electrode, such as a sintered metal electrode, that is attached to an inner surface of the distal end of the clamp member. The proximal ends of the first and second clamp members are handles, and the clamp members may be coupled at a pivot.

In one or more embodiments, the cutting element can be positioned so that a distal end of the cutting element is between the first and second clamp members, e.g., between the first and second porous electrodes. For this purpose, the cutting element may extend through an aperture defined by a clamp member, or within a gap defined between the first and second clamp members such that the cutting element can be moved within the aperture or gap.

Further, in one or more embodiments, the position of the cutting element may be adjusted by a user, e.g., by sliding the cutting element between a retracted position for coagulation of tissue and an extended position for engaging and cutting coagulated tissue.

BRIEF DESCRIPTION OF THE DRAWINGS

Embodiments of the invention will be described and explained with additional specificity and detail through the use of the accompanying drawings in which:

FIGS. 7A-F are partial distal end views of an apparatus illustrating how electrode and cutting element components of the apparatus are controlled to coagulate and cut tissue;

FIGS. 8A-F are partial side views of distal ends of an apparatus illustrating how electrode and a cutting element components of the apparatus are controlled to coagulate and cut tissue;

DETAILED DESCRIPTION OF ILLUSTRATED EMBODIMENTS

Figure 1A:
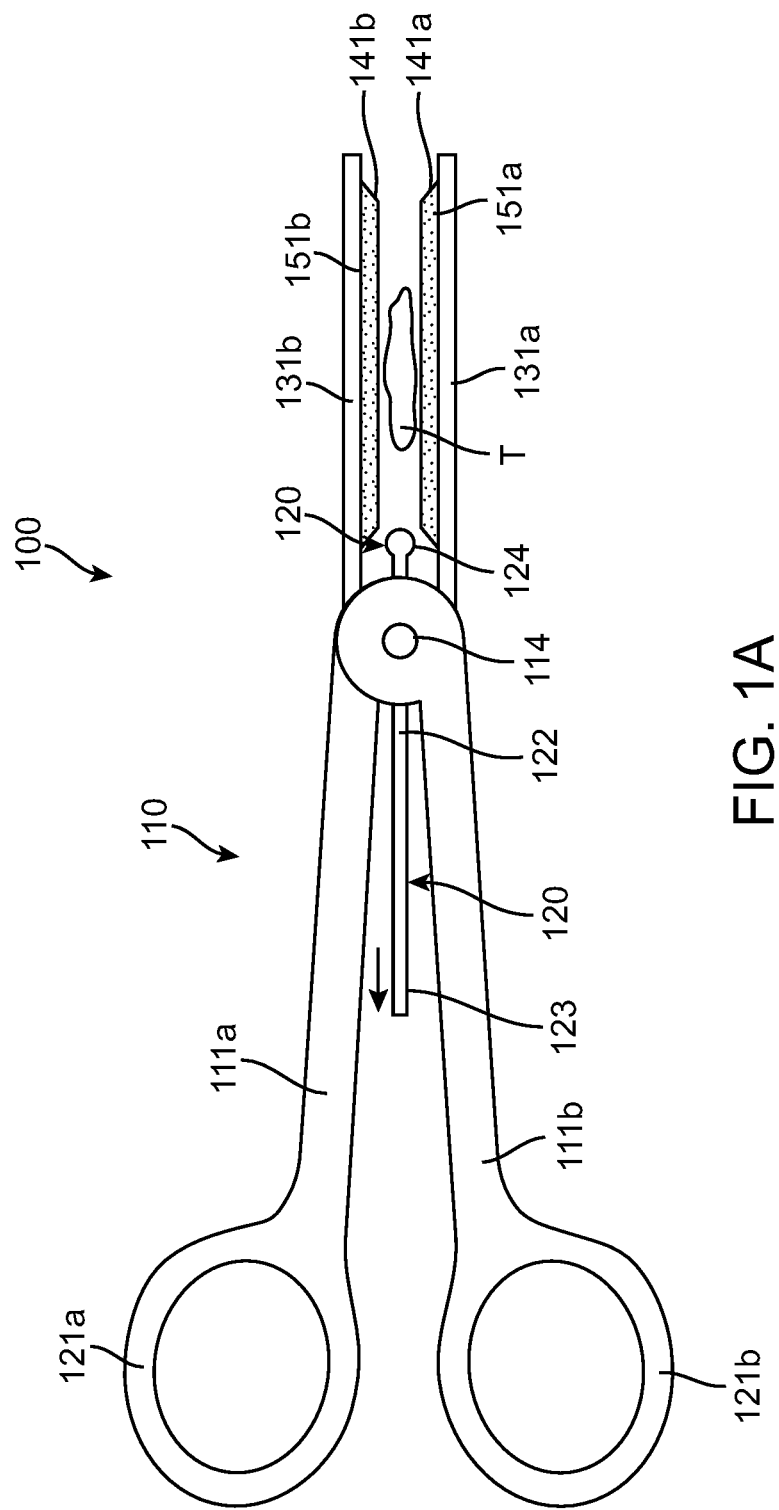
FIG. 1A illustrates a tissue coagulation and cutting apparatus constructed according to one embodiment having jaw members shown in a closed position.
Figure 1B:
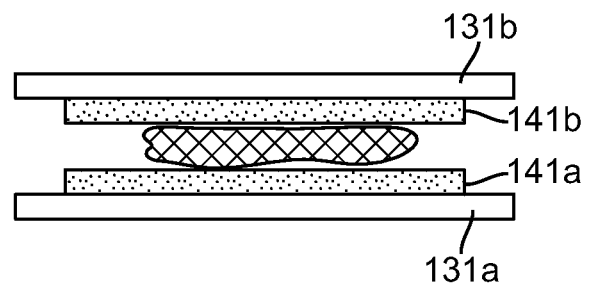
FIG. 1B is a partial distal end view of the apparatus shown in FIG. 1A.
Figure 1C:
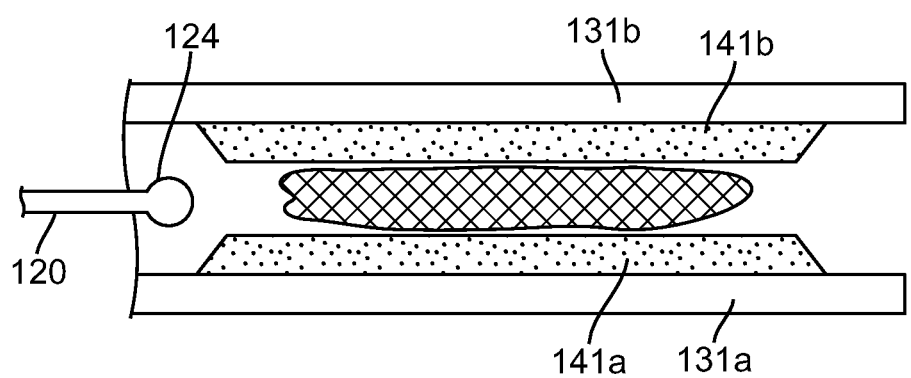
FIG. 1C is a partial side view of a distal end of the apparatus shown in FIG. 1A having jaw members shown in a closed position and a cutting element placed in a retracted position.
Figure 2A:
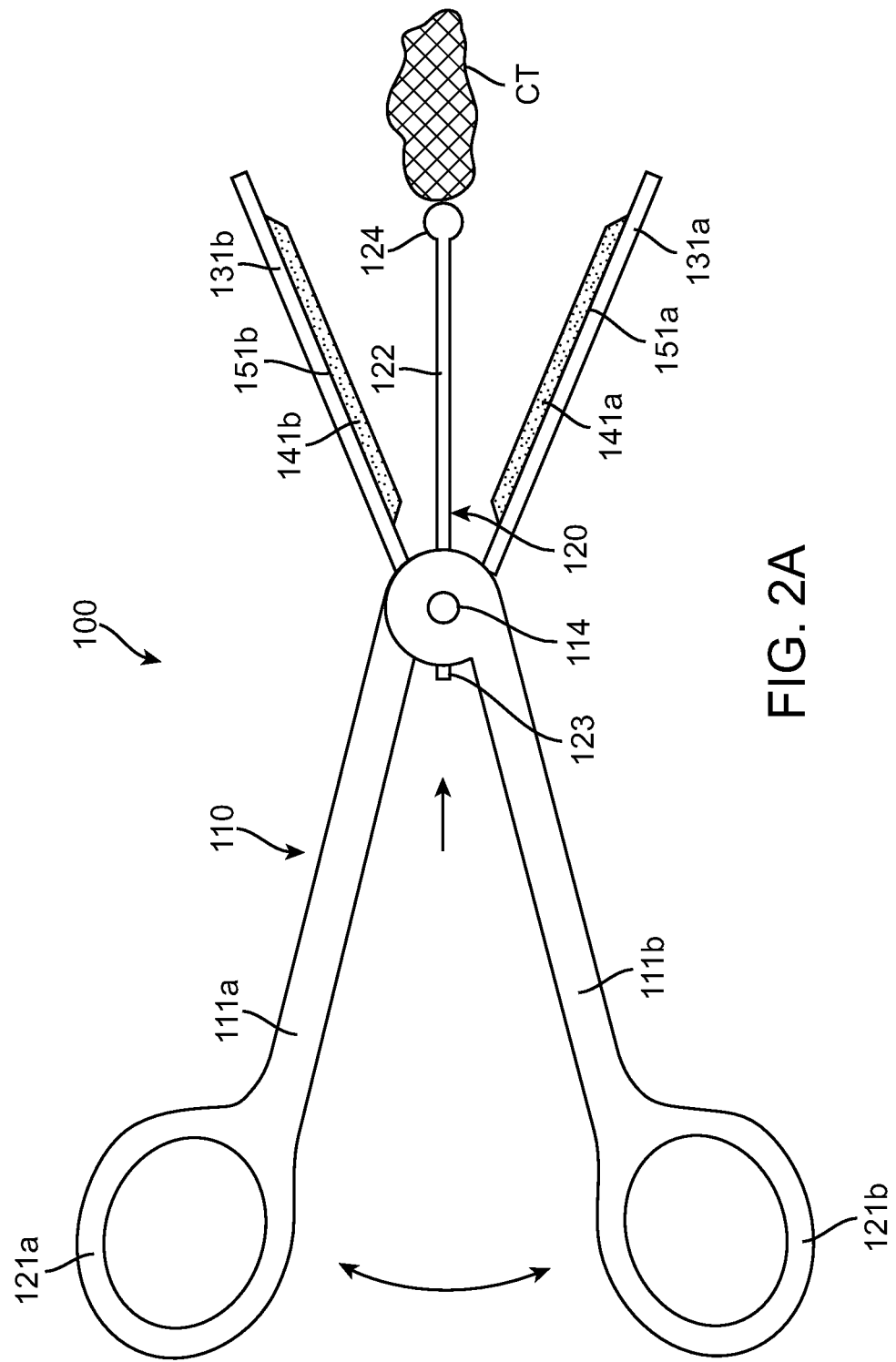
FIG. 2A illustrates the apparatus shown in FIG. 1A having jaw members shown in an open position and a cutting element placed in an extended position.
Figure 2C:
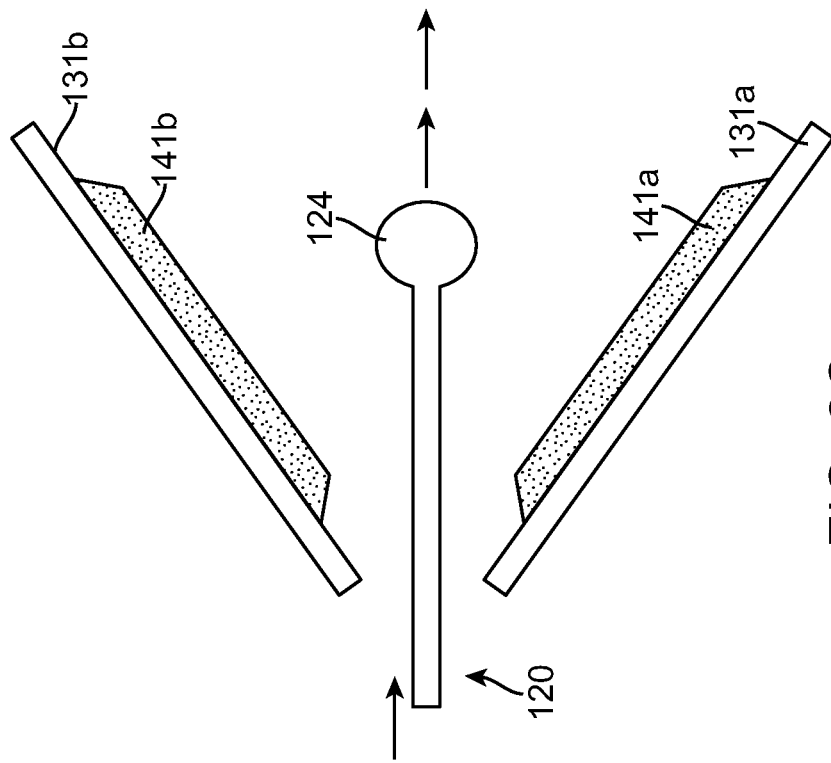
FIG. 2C is a partial side view of a distal end of the apparatus shown in FIGS. 2A-B.
Figure 2B:
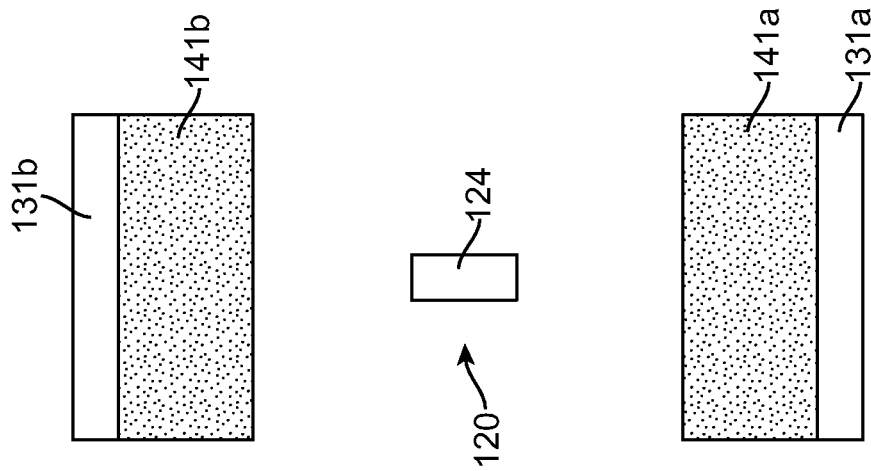
FIG. 2B is a partial distal end view of the apparatus shown in FIG. 2A.

Referring to FIGS. 1A-C and 2A-C, an electro-surgical apparatus 100 configured for both coagulating and cutting tissue constructed according to one embodiment includes a clamp element 110 and a moveable or adjustable cutting element 120 that is associated with the clamp element 110. Arrows adjacent to the cutting element 120 are provided to generally illustrate that the cutting element 120 can be adjusted or is positionable so that the cutting element 120 can be positioned between portions of the clamping element 110. The clamp element 110 is used to hold and coagulate tissue (as shown in FIGS. 1A-C), and the cutting element 120 is used to cut through a portion or all of the coagulated tissue (as shown in FIGS. 2A-C). The single electro-surgical apparatus 100 can advantageously be used to both coagulate and cut tissue, thereby reducing surgery times and eliminating the need to use separate instruments to perform coagulation and cutting functions.

According to one embodiment, the clamp element 110 includes first and second clamp members 111a and 111b (generally 111) that are connected to, and moveable or rotatable about, a pivot 114 or other connection. The clamp members 111 can be composed of a durable and rigid material, such as medical grade plastic, and can be ergonomically molded to allow a surgeon to more easily manipulate the apparatus 100. For example, proximal ends of respective clamping members 111a and 111b can be handles 121a and 121b (generally 121) that define apertures through which a surgeon's fingers can be inserted to allow the surgeon to manipulate the apparatus 100. The proximal ends or handles 121 of the clamping members 111 may also have other forms and may or may not include apertures.

Distal ends of respective clamping members 111a and 111b include first and second jaw members 131a and 131b (generally 131). In the illustrated embodiment, an inner surface 151a of the first jaw member 131a includes a first electrically conductive element or electrode 141a, and an inner surface 151b of the second jaw member 131b includes a second electrically conductive element or electrode 141b. The jaw members 131a and 131b and/or the electrodes 141a and 141b (generally 141) can be separate components that are removably attached to the clamping members 111a and 111b. Alternatively, the jaw members 131 and the electrodes 141 may be integrally formed with, be a part of, or be permanently attached to, the clamp members 111.

An electrode 141 may cover different areas and lengths of a jaw member 131. For example, in FIG. 1, the distal end of an electrode 141 extends partially to the distal end of a jaw member 131. The distal end of the electrode 141 may also extend to the distal end of the jaw member 131. Embodiments can be implemented with different jaw member 131/electrode 141 configurations to suit the particular apparatus configuration and surgical application. Further, in the illustrated embodiments, the electrodes 141 and 142 are the same shape and size. However, electrodes 141 of different shapes and sizes may also be utilized.

In the illustrated embodiment, the adjustable cutting element 120 includes an elongated body 122 having a proximal end 123 and a distal end 124. The cutting element 120 may be associated with the clamp element 110 in that the cutting element 120 extends through an aperture define by a portion of the clamp element 110. For example, the cutting element 120 may extend through an aperture defined by one of the clamping members 111, e.g., a clamping member 111, which may be fixed and does not rotate. Alternatively, the cutting element 120 may extend through a gap defined between two clamp members 111a and 111b.

According to one embodiment, the cutting element 120 may be in the form of an electrically conductive loop, such as a wire loop. The diameter of the distal or wire loop end 124, the wire material or conductivity, and/or the diameter of the loop can be selected to achieve desired cutting capabilities. In alternative embodiments, the distal end 124 of the cutting element 120 may be composed of other conductive materials and have other shapes and sizes. For example, rather than a loop, the distal end 124 may be in the form of a rounded or pointed tip, which may provide even greater current density if enhanced cutting capabilities are desired. Accordingly, the cutting element 120 shown in the Figures is one example of a suitable cutting element 120.

The tissue coagulation/cutting apparatus 100 may be manipulated by a surgeon to move the first and second clamping members 111, thereby closing and opening the jaw or clamping members 131 at the distal ends thereof. By manipulating the clamping members 111, tissue can be secured between, or released from, the electrodes 141.

When a portion of tissue is secured between the electrodes 141, electrical current may be applied to the electrodes 141 to seal and coagulate a portion of tissue, and a conductive solution, such as saline, may be applied to the area surrounding the tissue portion to advantageously reduce or prevent tissue charring. The adjustable cutting element 120 may then be positioned adjacent to or engage the coagulated tissue portion, or pushed into the coagulated tissue portion, to cut through a segment or all of the coagulated tissue portion when electrical current is applied to the cutting element 120.

The distal end 124 of the cutting element 120 extends between the electrodes 141 of the jaw members 131 and may advantageously be moved to different locations. In this manner, the distal end 124 of the cutting element 120 may be placed (e.g. slidably moved) to a certain position when the jaw members 131 are closed to coagulate tissue, and placed in another position when the coagulated tissue is to be cut, e.g., when the jaw members 131 are opened to release the coagulated tissue.

FIGS. 1A-C illustrate the cutting element 120 in a retracted position, and FIGS. 2A-C illustrate the cutting element 120 in an extended position, which may be between the jaw members 131 (as shown in FIG. 2C) or beyond the distal ends of the jaw members 131 (as shown in FIG. 2A). For clarity, the tissue portion is omitted from certain figures to illustrate the cutting element 120 and the jaw members 131. Thus, FIGS. 1A-C and 2A-C are provided to generally illustrate that the cutting element 120 can be adjusted (represented by arrows associated with the cutting element 120) and placed in different positions depending on whether the tissue portion is to be coagulated or cut.

For example, referring to FIGS. 1A-C, the cutting element 120 may be placed in a retracted position when the jaw members 131 carrying the electrodes 141 are closed or substantially closed to hold and coagulate tissue held there between. When the jaw members 131 are opened, as shown in FIGS. 2A-C, e.g., following coagulation of tissue, the cutting element 120 can be slidably moved so that it extends between the electrodes 141, and the distal cutting tip 124 is positioned to cut a segment or all of the tissue that was coagulated. Electrodes 141 having larger surface areas (and lower current densities) are used to hold and coagulate tissue, whereas a smaller cutting element 120 (having greater current density) may be positioned and adjusted as needed to cut through coagulated tissue. Thus, embodiments advantageously provide a single electro-surgical instrument having both coagulation and cutting capabilities.

As shown in FIGS. 2A-C, the cutting element 120 is engaged when the jaw members 131 are open. In an alternative embodiment, referring to FIG. 3, the cutting element 120 may be used to cut tissue when the jaw members 131 are substantially closed if sufficient space 160 is provided between the jaw members 131 to allow the distal end 124 of the cutting element 120 to be inserted into the space 160. With this configuration, tissue can be held between the electrodes 141 and coagulated while, at the same time, the cutting element 120 pushes into and cuts the tissue after or during coagulation. Thus, embodiments can be implemented based on the cutting element 120 being advanced forward to cut tissue when the jaw members 131 are open, or when they are closed.

Figure 4:
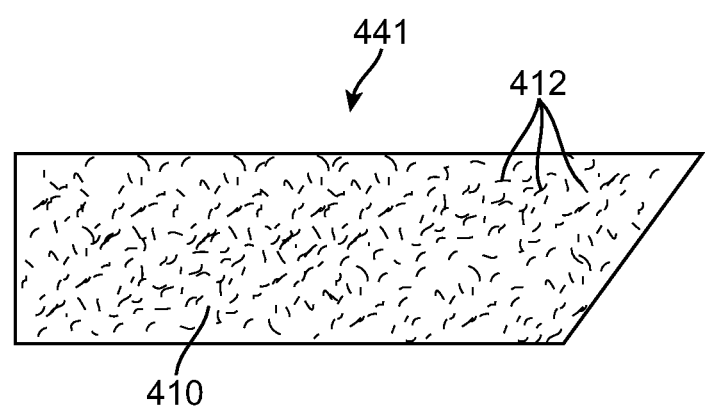
FIG. 4 is a close-up side view of a porous electrode for use with various embodiments.

Referring to FIG. 4, according to one embodiment, an electrode 141 may be a porous electrode. A porous electrode 441 suitable for use with embodiments includes a porous structure 410 having interconnected pores 412. The porous structure 410 allows fluid to pass around the porous electrode 441 on the outer surface of the electrode 441 and to pass through the porous electrode 441, thereby facilitating uniform distribution of an electrically conductive fluid into the tissue during the coagulation process. In addition to providing a more uniform distribution of fluid, the porous structure 410 is less apt to stick to the surfaces of the porous electrode 441.

The porosity of the porous structure 410, as defined by the pore 412 volume over the total volume of the structure 410, may be in the 20-80 percent range, e.g., about 30-70 percent. In one embodiment, the pores 412 are interconnected in a random, tortuous, interstitial arrangement in order to maximize the porosity of the porous electrodes 441. The porous structure 410 may be microporous, in which case, the effective diameters of the pores 412 are about 0.05-20 microns. The porous structure 410 may also be macroporous, in which case, the effective diameters of the pores 512 are about 20-2000 microns. According to one embodiment, the size of the pores 512 is about 1-50 microns. Naturally, the higher the porosity, the more freely the fluid will flow through the porous electrodes 441. Thus, the porosity of the porous structure 410 will ultimately depend on the desired flow of the fluid. Of course, the porous structure 410 should not be so porous as to unduly sacrifice the structural integrity of the porous electrodes 441.

The porous structure 410 is preferably composed of a metallic material, such as stainless steel, titanium, or nickel-chrome. While each porous electrode 441 is preferably composed of an electrically conductive material, the porous electrode 441 may alternatively be composed of a conductive non-metallic material, such as porous polymer or ceramic. While the porous polymers and ceramics are generally non-conductive, they may be used to conduct electrical energy to the tissue by virtue of the conductive fluid within the interconnected pores 412.

For purposes of ease in manufacturability, the entirety of the electrodes 441 is composed of the porous structure 410. Alternatively, only the portion of the electrodes 441 that will be adjacent the ablation region (e.g., the distal portion of the electrodes 441) is composed of the porous structure 410. Preferably, the porous structure 410 provides for the wicking (i.e., absorption of fluid by capillary action) of fluid into the pores 412 of the porous structure 410. To promote the wicking of fluid into the porous structure 410, the porous structure 410 may be hydrophilic.

In one embodiment, the porous structure 410 is formed using a sintering process, which involves compacting a plurality of particles (e.g., a blend of finely pulverized metal powers mixed with lubricants and/or alloying elements) into the shape of the porous electrode 441, and then subjecting the blend to high temperatures. When compacting the particles, a controlled amount of the mixed powder is automatically gravity-fed into a precision die and is compacted, usually at room temperature at pressures as low as 10 or as high as 60 or more tons/inch$^2$ (138 to 827 MPa), depending on the desired porosity of the porous electrode 441. The compacted powder will have the shape of the porous electrode 441 once it is ejected from the die, and will be sufficiently rigid to permit in-process handling and transport to a sintering furnace. Other compacting and alternative forming methods can also be used, such as powder forging, isostatic pressing, extrusion, injection molding, and spray forming.

During sintering, the unfinished porous electrode 441 is placed within a controlled-atmosphere furnace, and is heated to below the melting point of the base metal, held at the sintering temperature, and then cooled. The sintering transforms the compacted mechanical bonds between the power particles to metallurgical bonds. The interstitial spaces between the points of contact will be preserved as pores 412. The amount and characteristics of the porosity of the structure 410 can be controlled through powder characteristics, powder composition, and the compaction and sintering process.

The porous structures 410 can be made by methods other than sintering. For example, the pores 412 may be introduced by mechanical perforation, by the introduction of the pore 412 producing agents during a matrix forming process, or through various phase separate techniques. Also, the porous structure 410 may be composed of a ceramic porous material with a conductive coating deposited onto the surface, e.g., by using ion beam deposition or sputtering. While FIG. 4 and the above description relates to sintered metal porous electrodes, it should be understood that other porous electrodes can also be utilized.

FIGS. 5-11 further illustrate how the apparatus 100 described with reference to FIGS. 1A-4 may be utilized and how the apparatus 100 may be integrated within a tissue coagulation/cutting system 500. For purposes of illustration and explanation, the remaining figures are described with reference to the electrodes 141a and 141b being sintered metal porous electrodes 441a and 441b (generally 441).

Figure 5:
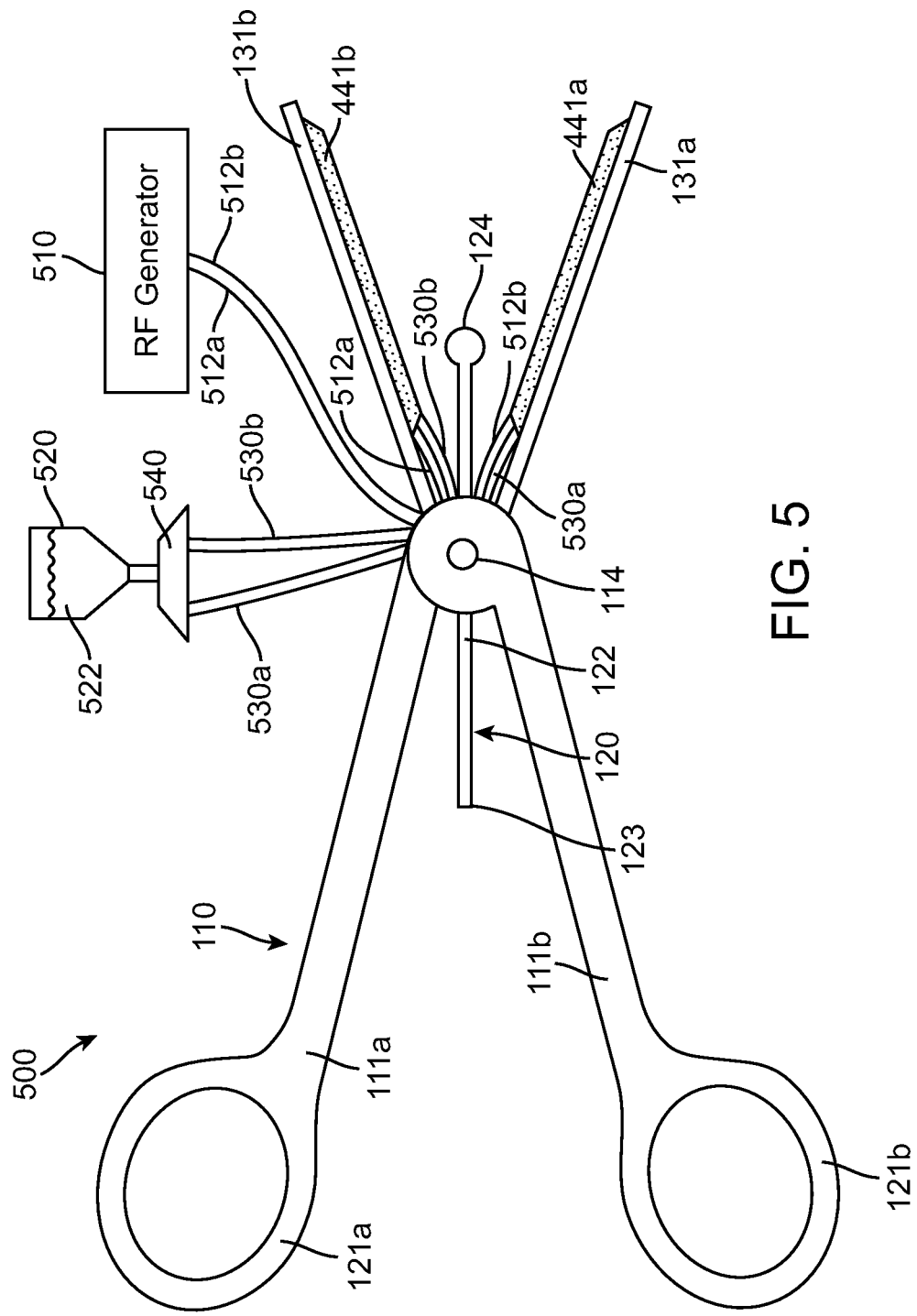
FIG. 5 illustrates a tissue resection system having an apparatus for coagulating and cutting tissue according to one embodiment.
Figure 6:
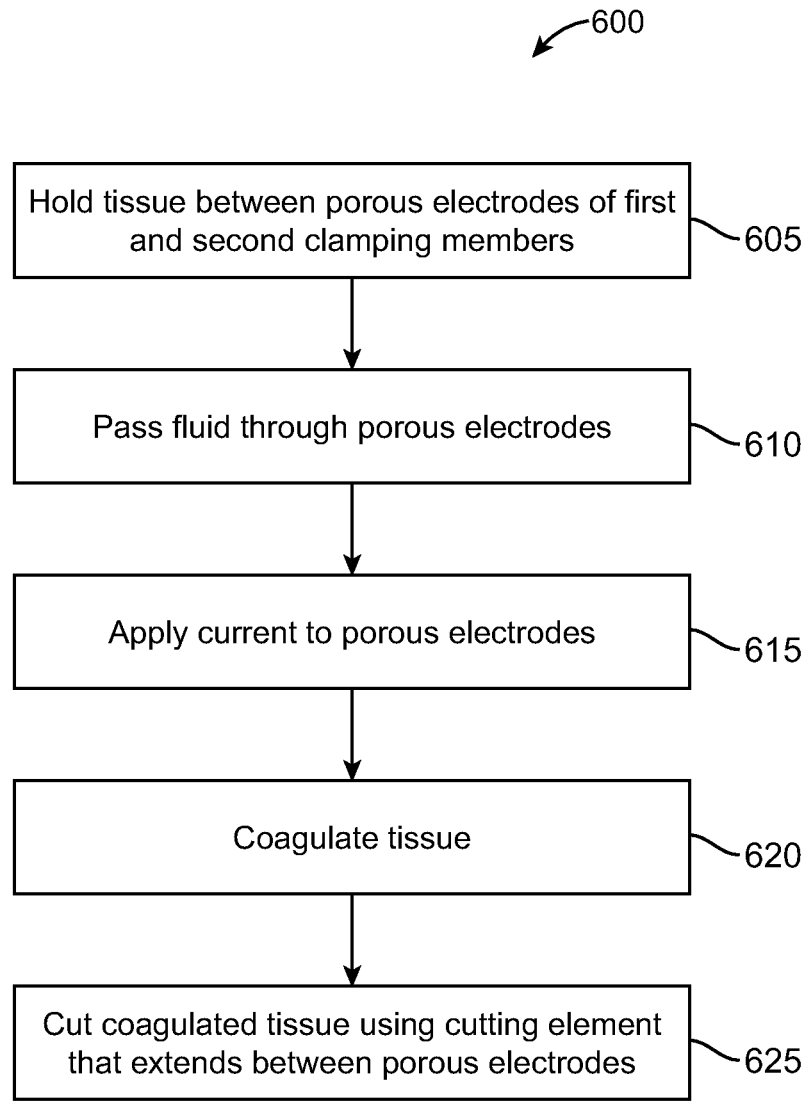
FIG. 6 is a flow chart of a method of coagulating and cutting tissue with the same surgical instrument according to another embodiment.

Referring to FIG. 5, a surgical system 500 according to one embodiment includes the tissue coagulation/cutting apparatus 100 discussed above with reference to FIGS. 1A-4, an ablation energy source 510, such as a RF generator, and a source 520 of electrically conductive fluid 522. The RF generator 510 is configured for supplying RF energy to the porous electrodes 441 in a controlled manner. One or more electrical leads or cables 512 provide an electrically conductive path for the RF energy from the RF generator 510 to the porous electrodes 441 and to the tissue to be coagulated and cut or resected.

One suitable RF generator 510 that can be used with embodiments is a conventional RF power supply that operates at a frequency in the range from 200 KHz to 9.5 MHz, with a conventional sinusoidal or non-sinusoidal wave form. Such power supplies are available from many commercial suppliers, such as Valleylab, Aspen, and Bovie. Most general purpose electro-surgical power supplies, however, operate at higher voltages and powers than would normally be necessary or suitable for tissue ablation. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF 2000® and RF 3000®.

One fluid source 520 that can be used with embodiments is a saline bag, configured for supplying the electrically conductive fluid 522 (e.g., saline) to the porous electrodes 441 via fluid lumens 530a and 530b (generally 530). In the illustrated embodiment, the fluid source 520 takes the form of a saline bag connected to the fluid lumens 530 via a Y-conduit 540, and the fluid lumens 530 are in fluid communication with the pores 412 of the porous structure 410 of the electrodes 441. For example, the fluid lumens 530 may be attached or coupled to the porous electrodes 441 using a suitable coupler, connector or bonding material. The saline bag 520 may be a conventional and is of a suitable size, e.g., 200 ml. In the illustrated embodiment, the saline is 0.9% saline. Thus, it can be appreciated the saline bag 520 can be raised above the patient a sufficient height to provide the head pressure necessary to convey the saline 522 under pressure through the Y-conduit 540, into the fluid lumens 530, and out of the porous electrodes 441. Alternatively, rather than a saline bag, the fluid source 520 may take the form of a pump assembly or a syringe.

The pervasiveness of the pores 412 allows the conductive fluid 522 to freely flow from the fluid source 520 through the fluid lumens 530, through the thickness of the porous electrodes 441, and out to the adjacent tissue to be coagulated. Significantly, this free flow of conductive fluid 522 will occur even if several of the pores 512 have been clogged with material, such as tissue.

It should be understood that although FIG. 5 illustrates a system 500 having separate fluid lumens 530 and electrical leads 512, embodiments can be implemented by incorporating fluid lumens 530 and electrical leads 512 into a shaft, lumen, collar or other structure that bundles various connection components together. Further, FIG. 5 illustrates fluid lumens 530 and electrical leads 512 that are connected or attached to porous electrodes 441 through or near the connection or pivot 114, but the fluid lumens 530 and leads 512 can be attached to the porous electrodes in different manners.

Having described the general structure and function of the tissue resection system 500, its operation in resecting tissue will be described. The tissue may be located anywhere in the body where resection may be beneficial. Most commonly, the tissue will contain a solid tumor within an organ of the body, such as the liver, kidney, pancreas, breast, prostrate (not accessed via the urethra), and the like. In this case, an unhealthy tissue portion such as a cancerous portion containing a tumor, e.g., a lobe of a liver, may be resected from the healthy portion of the tissue. In the preferred method, access to the tissue may be accomplished through a surgical opening to facilitate movement of the apparatus 100 within the patient as well as to facilitate removal of the resected tissue from the patient. However, access to the tissue may alternatively be provided through a percutaneous opening, e.g., laparoscopically, in which case, the tissue resection probe can be introduced into the patient through a cannula, and the removed tissue may be minsilated and aspirated from the patient through the cannula.

One manner in which embodiments can be utilized is illustrated in FIGS. 6, 7A-F and 8A-F. FIGS. 7A-F are partial distal end views of a tissue coagulation/cutting apparatus 100 with reference to an x-y-z coordinate system. The jaw members 131 are shown as being movable in the "y" direction, and the cutting element 120 is movable in the "z" direction. FIGS. 8A-F further illustrate partial side views of a distal end of a tissue coagulation/cutting apparatus 100 for coagulating and cutting tissue with reference to an x-y-z coordinate system in which the jaw members 131 are movable in the "y" direction, and the cutting element 120 is movable in the "x" direction.

A method 600 of coagulating and cutting tissue with a single surgical instrument or apparatus 100 according to one embodiment includes holding or grasping a portion of tissue to be resected between the porous electrodes 141 in step 605. The porous electrodes 141 are carried by respective jaw members 131 of clamp members 111 and connected to the RF generator 510 via associated leads or connectors 512. As shown in FIGS. 7A and 8A, the clamp members 111 are manipulated by a surgeon so that the distal ends of the clamp members 111 or the jaw members 131 are initially opened to permit the tissue portion to be positioned between the porous electrodes 141. Thus, the porous electrodes 141 engage the tissue portion, and it is not necessary that the cutting element 120 be deployed at this time. As shown in FIGS. 7B and 8B, the clamp members 111 are moved by a surgeon, thereby closing the jaw members 131 and the porous electrodes 141 around the tissue portion to be resected.

In step 610, a conductive fluid 522, such as saline, is passed through the porous electrodes 141. For this purpose, the fluid source 520 and associated conduit 540 are connected to the fluid lumens 530, and the saline 522 is conveyed under positive pressure, through the conduit 540, and into the fluid lumens 530. In this manner, the saline 522 contacts the porous electrodes 441 and is conveyed out of the pores 412 of the porous electrodes 441 and into contact with the outer surface of the porous electrodes 441.

In step 615, the RF generator 510 is activated, and electrical current is applied to the porous electrodes 441, and in step 620, the tissue portion held between the porous electrodes 141 is coagulated. This is further illustrated in FIGS. 7C and 8C.

Figure 3:
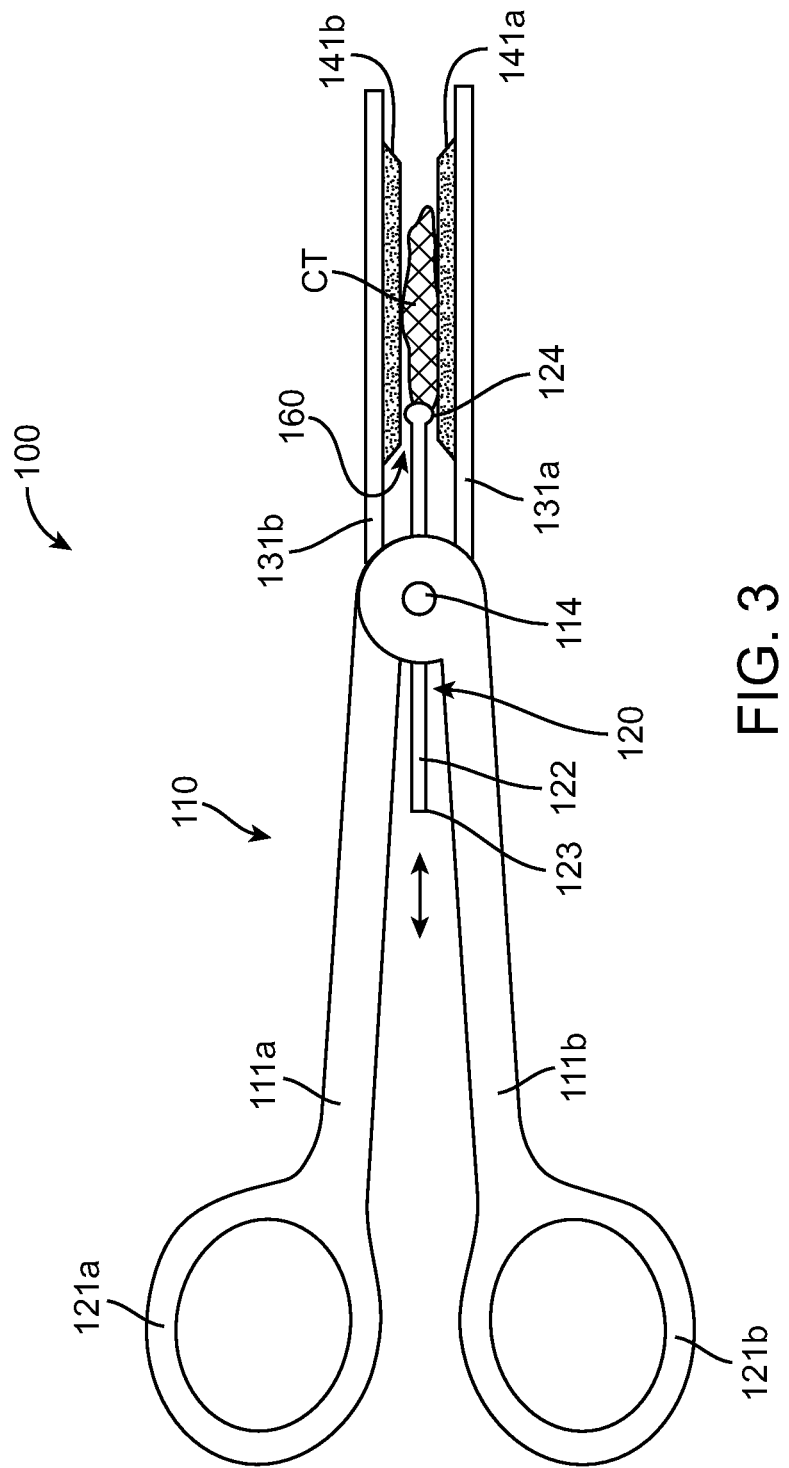
FIG. 3 illustrates the apparatus shown in FIG. 1 in which a cutting element extends between closed jaw members to cut coagulated tissue according to another embodiment.

In step 625, a segment or all of the coagulated tissue is severed by positioning a cutting element adjacent to or against coagulated tissue and applying electrical current to the cutting element 120 (from the same RF generator 510 or a different generator). Coagulated tissue may be cut after the jaw members 131 are opened (as shown in FIGS. 2A-C), or while the jaw members 131 remain closed (as shown in FIG. 3).

More particularly, referring to FIGS. 7D and 8D, the jaw members 131 may be opened to release the coagulated tissue portion after a predetermined amount of time or after a desired degree of coagulation. Referring to FIGS. 7E, 7F, 8E and 8F, the cutting element 120 may be slidably moved from its initial position to an extended position to be adjacent to or contact the coagulated tissue, thereby cutting or slicing through a segment or all of the coagulated tissue when electrical current is applied to the cutting element 120.

Although, FIGS. 6, 7A-F and 8A-F illustrate a specific sequence of steps, it should be understood that various steps may be performed in different orders, at different times, or at the same time. For example, electrically conductive fluid 522 may be passed through the porous electrodes 441 while electrical current is applied to the electrodes 441 and/or to the cutting element 120. Additionally, tissue can be coagulated and then subsequently cut, or coagulated at the same time or at about the same time that tissue is cut. Additionally, different amounts or segments of coagulated tissue can be cut. Further, the cutting element 120 can be applied to coagulated tissue while current is applied to the electrodes 141. Components can also be connected in different orders. Thus, the particular sequence of steps illustrated in these figures is provided as an example sequence of one method of coagulating and cutting tissue.

As shown in FIGS. 1A-8F, the cutting element 120 extends between the porous electrodes 441 carried by the jaw members 131 and can be moved in different ways and by different degrees. The manner and degree of movement may, for example, depend on the length of the cutting element 120, the location of the coagulated tissue, and other structural aspects of a tissue coagulation/cutting apparatus 100.

Figure 9A:
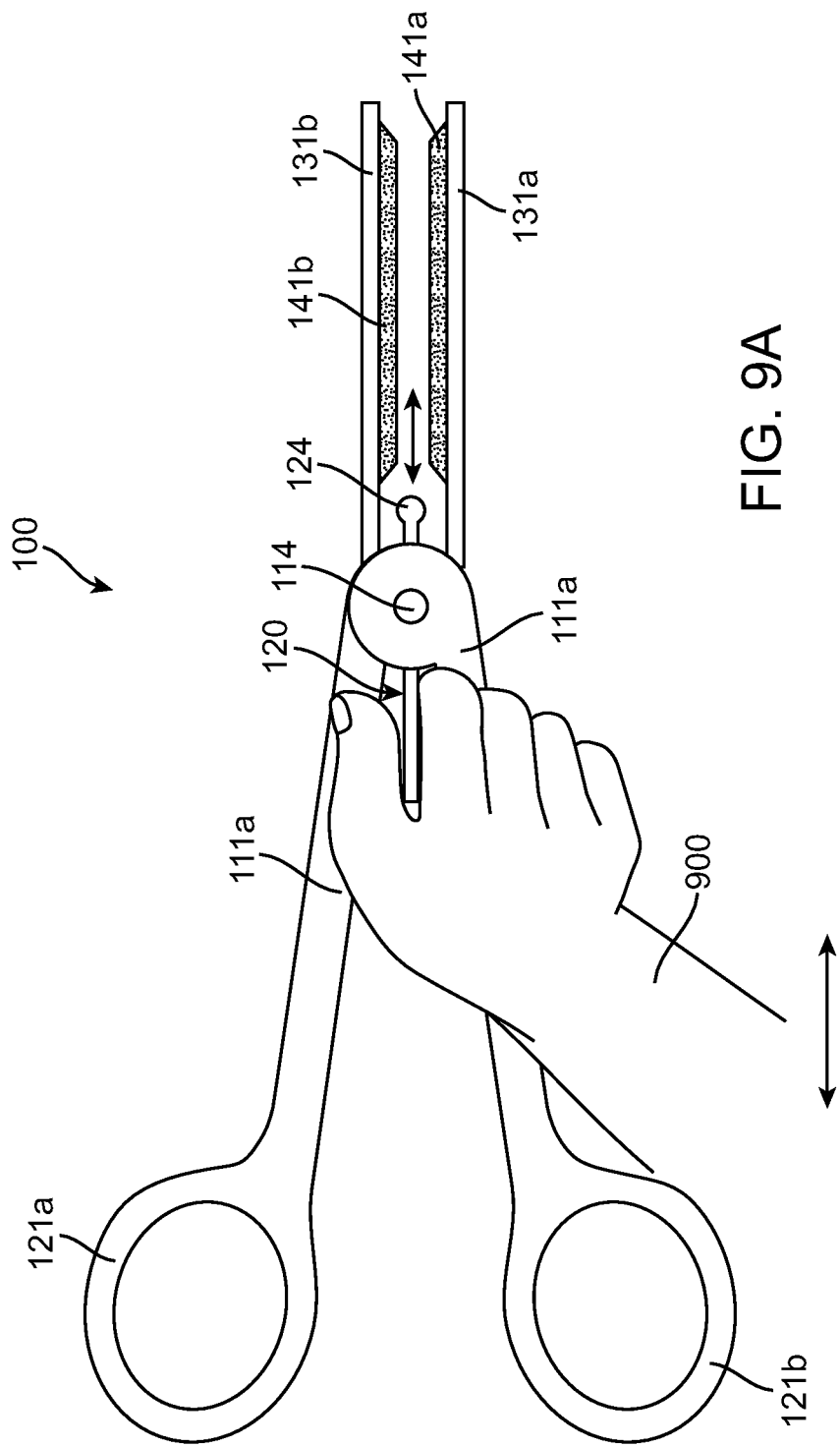
FIG. 9A illustrates a tissue coagulation and cutting apparatus having a manually adjustable cutting element according to one embodiment.
Figure 9B:
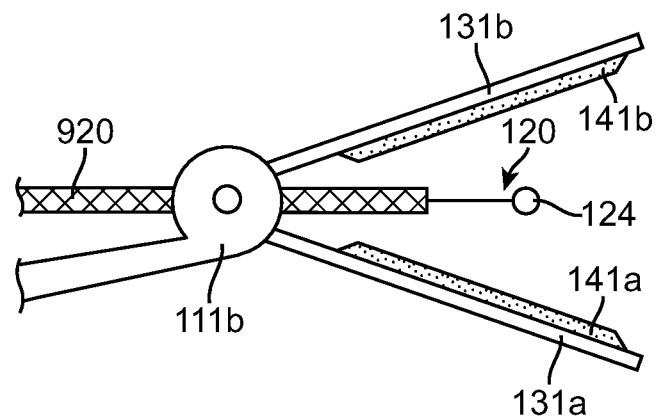
FIG. 9B is a partial side view of a distal end of coagulation and cutting apparatus having a manually adjustable cutting element including an insulative coating that can be grasped by a surgeon.
Figure 9C:
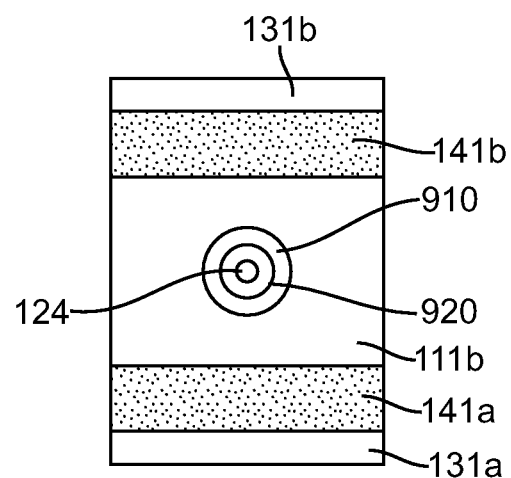
FIG. 9C is a partial distal end view of the apparatus shown in FIG. 9B.

According to one embodiment, as shown in FIGS. 9A-C, the cutting element 120 can be manually moved or adjusted by a surgeon 900 in order to place the cutting element 120 in the desired position to cut coagulated tissue. For this purpose, during or after tissue coagulation, the surgeon 900 may grasp the cutting element 120 or an insulative coating or cover 920 surrounding the cutting element 120. The coated cutting element 120 may extend and be slidably moved through an aperture or gap 910 formed through or between one or more clamp members 111, e.g., clamp member 111b as shown in FIG. 9C. A surgeon may pull the coated cutting element 120 so that the distal end 124 of the cutting element 120 is pulled away from the jaw members 131 and away from tissue. This may allow the jaw members 131 to be closed (e.g., as shown in FIG. 2) so that electrical current supplied by the RF generator 150 can be conveyed to the porous electrodes 441 to coagulate tissue. The jaw members 131 may be opened to release coagulated tissue, and the surgeon can push the coated cutting element 120 forward so that the distal end 124 of the cutting element 120 is pushed into the coagulated tissue to cut or slice through a segment or all of the coagulated tissue.

According to one embodiment, the cutting element 120 is freely moveable and can be placed in a retracted position, an extended position, and any position between the retracted and extended positions. In these embodiments, the position of the cutting element 120 may be manually maintained and adjusted by the surgeon, and the cutting element 120 can be moved without mechanical restriction. According to another embodiment, the body 122 of the cutting element 120 can have detents, catches, latches, grooves or other suitable mechanisms or components (not shown) that may be used to temporarily maintain or resist movement of the cutting element 120 to remain in a position selected by the surgeon.

As a further alternative, the coated cutting element 120 can extend through a port or aperture 910 that is made of a suitable material such that the port or aperture is of sufficient size so as to provide sufficient frictional force to temporarily maintain the cutting element 120 in a particular position after the cutting element 120 is placed in that position by a surgeon. When the cutting element 120 is to be moved, the surgeon can push or pull the body 122 of the cutting element 120 by applying sufficient force to overcome the friction force that maintained the cutting element 120 in its previous position and move the cutting element 120 to a new position.

Figure 10:
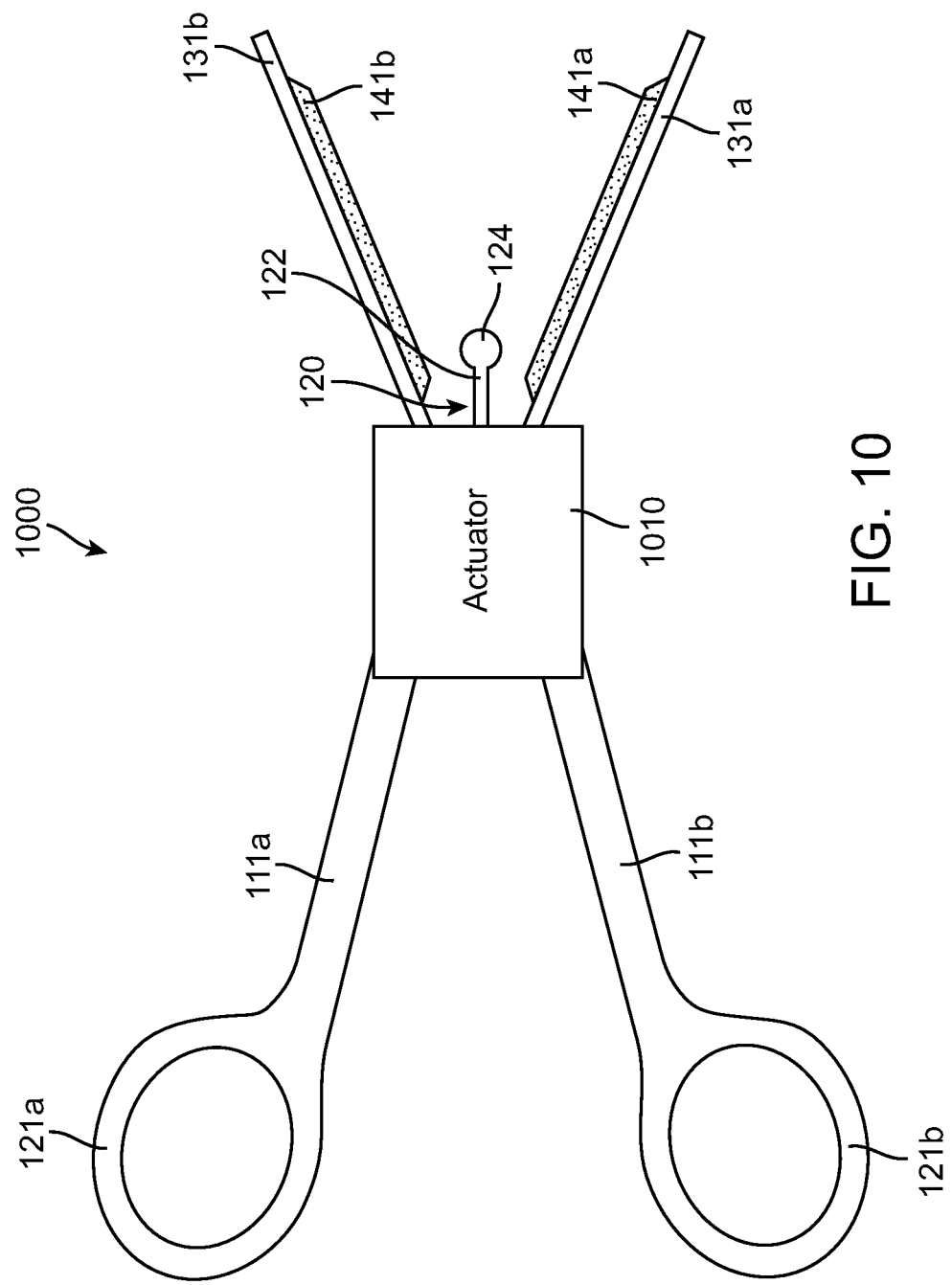
FIG. 10 illustrates a tissue coagulation and cutting apparatus having an actuation device for moving an adjustable cutting element to different positions according to another embodiment.

Referring to FIG. 10, in an alternative embodiment, a system 1000 includes a tissue coagulation/cutting apparatus 100 as described above and, in addition, an actuator 1010, such as a mechanical or electro-mechanical actuator, for effecting movement of the cutting element 120. In one embodiment, the actuator 1010 can be configured to move the cutting element 120 based on a position or rotational movement of the clamping members 111, jaw members 131 and/or porous electrodes 141. For example, the actuator 1010 can be a mechanical actuator having one or more gears coupled to the clamping members 111 and the cutting element 120 so that movement of the clamping members 111 by a surgeon drives one or more gears to move laterally move the cutting element 120. The surgeon can manipulate the clamping members 111 to laterally move the cutting element 120 rather than manually moving the cutting element 120.

According to one embodiment, the actuator 1010 can be configured to move the cutting element 120 in response to a position requested by a surgeon. For example, the actuator 1010 can be a motorized mechanism that includes forward and reverse buttons that can be selected by a surgeon to extend or retract the cutting element 120.

In a further alternative embodiment, the clamping members 111 and/or jaw members 131 can include sensors that indicate the relative or absolute position of the clamping members 111, jaw members 131 and/or porous electrodes 141. The actuator 1010 may include a controller or processor that receives sensor data and generates an output corresponding to the position of the cutting element 120. The actuator 1010 may then be configured to move the cutting element 120 based on the output.

For example, when the angle between the jaw members 131 is zero or below a pre-determined value, the actuator 1010 may receive the corresponding sensor data and in response thereto, generate an output that drives a mechanism to move or place the cutting element 120 in a retracted position. As the surgeon moves the clamping members 111, thereby opening the jaw members 131, the angle between the jaw members 131 increases. Data from the sensors representing the larger angle may be provided to the actuator 1010, which moves or places the cutting element 120 accordingly.

According to another embodiment, movement of the cutting element 120 may be continuous and correspond (linearly or non-linearly) to a corresponding movement of the clamping members 111. For example, a surgeon may freely move the cutting element 120, or if an actuator 1010 is used, the cutting element 120 can be moved for a given change in the position or movement of the clamping members 111 or other components. Thus, in both of these manual and actuator embodiments, there is cutting element 120 movement that corresponds to movement of the clamping members 111.

In an alternative embodiment, movement or the position of the cutting element 120 may not correspond to a given movement of a clamping element 111. There may be instances when movement of the clamping members 111 does not result in movement of the cutting element 120, but other times when movement of the clamping members 111 does result in movement of the cutting element 120. For example, the cutting element 120 may be placed in a retracted position when the jaw members 131 are closed to hold tissue. The cutting element 120 can be maintained in that retracted position until the clamping members 111 and jaw members 131 are moved or rotated by a certain degree, at which point the actuator 1010 can eject the cutting element 120 from the initial, retracted position to an extended position. Persons skilled in the art will appreciate that various types of actuator 1010 devices can be utilized, and that the actuators 1010 described above are provided to describe examples of how embodiments can be implemented.

Although particular embodiments have been shown and described, it should be understood that the above description is not intended to limit the scope of embodiments since various changes and modifications may be made without departing from the scope of the claims. Thus, embodiments are intended to cover alternatives, modifications, and equivalents that fall within the scope of the claims.

What is claimed is:

1. An electro-surgical apparatus for coagulating and cutting tissue, comprising:
   a first clamp member having a proximal end, a distal end, an inner surface, and an outer surface, wherein a first porous electrode is attached to the inner surface of the distal end of the first clamp member;
   a second clamp member coupled to the first clamp at a pivot, at least one of the first and second clamp members being moveable about the pivot, the second clamp member having a proximal end, a distal end, an inner surface, and an outer surface, wherein the second porous electrode is attached to the inner surface of the distal end of the second clamp member;
   an aperture or gap passing through the pivot; and
   a cutting element passing through the aperture or gap, wherein a position of the cutting element being adjustable for cutting the coagulated tissue portion when electrical current is conducted through the cutting element and the coagulated tissue portion.

2. The electro-surgical apparatus of claim 1, wherein the first and second clamp members and the cutting element are configured to coagulate the tissue portion and subsequently cut coagulated the coagulated tissue portion.

3. The electro-surgical apparatus of claim 1, wherein the first and second clamp members and the cutting element are configured to coagulate and cut the tissue portion simultaneously or at about the same time.

4. The electro-surgical apparatus of claim 1, wherein the first and second clamp members and the cutting element are configured to respectively coagulate and cut a blood vessel.

5. The electro-surgical apparatus of claim 1, wherein the proximal ends of the first and second clamp members are handles.

6. The electro-surgical apparatus of claim 1, wherein a distal end of the adjustable cutting element is positionable between the first and second clamp members.

7. The electro-surgical apparatus of claim 1, wherein a distal end of the adjustable cutting element is positionable between the first and second porous electrodes.

8. The electro-surgical apparatus of claim 1, wherein the porous electrodes are sintered metal electrodes.

9. The electro-surgical apparatus of claim 1, wherein the adjustable cutting element is a wire cutting element.

10. The electro-surgical apparatus of claim 1, wherein the cutting element can be controlled to cut a segment of the coagulated tissue portion.

11. The electro-surgical apparatus of claim 1, wherein the cutting element can be controlled to cut the entire coagulated tissue portion.

12. The electro-surgical apparatus of claim 1, wherein the aperture or gap passing through the pivot is oriented generally perpendicular to the axis of the pivot.

* * * * *